(12) United States Patent
Wang et al.

(10) Patent No.: US 9,551,674 B1
(45) Date of Patent: Jan. 24, 2017

(54) METHOD OF PRODUCING AN UN-DISTORTED DARK FIELD STRAIN MAP AT HIGH SPATIAL RESOLUTION THROUGH DARK FIELD ELECTRON HOLOGRAPHY

(71) Applicant: GLOBALFOUNDRIES Inc., Grand Cayman (KY)

(72) Inventors: Yun-Yu Wang, Poughquag, NY (US); John Bruley, Poughkeepsie, NY (US)

(73) Assignee: GlobalFoundries, Inc., Grand Cayman (KY)

( * ) Notice: Subject to any disclaimer, the term of this patent is extended or adjusted under 35 U.S.C. 154(b) by 0 days.

(21) Appl. No.: 14/928,605

(22) Filed: Oct. 30, 2015

(51) Int. Cl.
*G01N 23/00* (2006.01)
*G01N 23/04* (2006.01)

(52) U.S. Cl.
CPC ........... *G01N 23/04* (2013.01); *G01N 2223/03* (2013.01); *G01N 2223/607* (2013.01)

(58) Field of Classification Search
CPC .............. G01N 23/04; G01N 2223/607; G01N 2223/03
USPC ................................. 250/306, 307, 310, 311
See application file for complete search history.

(56) References Cited

U.S. PATENT DOCUMENTS

| | | | | |
|---|---|---|---|---|
| 7,015,469 | B2 * | 3/2006 | Wang ....................... | H01J 37/26 250/307 |
| 7,102,145 | B2 * | 9/2006 | Domenicucci ........... | G03H 5/00 250/306 |
| 8,193,494 | B2 | 6/2012 | Harada et al. | |
| 8,378,299 | B2 | 2/2013 | Frosien | |
| 8,502,143 | B2 | 8/2013 | Hytch et al. | |
| 8,598,526 | B2 | 12/2013 | Benner | |
| 8,772,714 | B2 | 7/2014 | Yamazaki | |
| 2014/0197312 | A1 * | 7/2014 | Harada .................... | H01J 37/26 250/307 |

OTHER PUBLICATIONS

Wang, Yun-Yu; Domenicucci, A; Li, J; Bruley, J.; Variable Magnification Dual Lens Electron Holography for Semiconductor Junction Profiling and Strain Mapping; 2012 Elsevier B.V., Ultramicroscopy 124 pp. 117-129.

(Continued)

*Primary Examiner* — Michael Maskell
(74) *Attorney, Agent, or Firm* — DeLio, Peterson & Curcio, LLC; Peter W. Peterson (57) ABSTRACT

An inline dark field holographic method for measuring strain in a semiconductor or other crystalline material using a transmission electron microscope having an electron gun for passing an electron beam through strained and unstrained specimens. A condenser mini-lens between the magnetic tilting coil and the specimens increases defection of the beam at an angle with prior to passing through the pair of specimens. The first objective lens forms a virtual image of each of the specimens and the second objective lens focuses the virtual images of each of the specimens at an intermediate image plane to form intermediate images of each of the specimens. The biprism creates the interference pattern between the specimens is formed at the image plane, which may then be viewed to determine the degree of strain of the strained specimen and provides a coma-free strain map with minimal optical distortion.

20 Claims, 7 Drawing Sheets

(56) References Cited

OTHER PUBLICATIONS

Wang, Yun-Yu; Domenicucci, A; Li, J; Bruley, J.; Dual-Lens Holography for Junction Profiling and Strain Mapping of Semiconductor Devices; Microscopy Today, May 2014, pp. 2-7.

Hytch, M.; Gatel, C.; Houdellier, F.; Snoeck, E. and Ishizuka, K.; Darkfield Electron Holography for Strain Mapping at the Nanoscale; Microscopy and Analysis-Nanotechnology Issue Nov. 2012, pp. 6-10.

\* cited by examiner

METHOD OF PRODUCING AN UN-DISTORTED DARK FIELD STRAIN MAP AT HIGH SPATIAL RESOLUTION THROUGH DARK FIELD ELECTRON HOLOGRAPHY

BACKGROUND OF THE INVENTION

1. Field of the Invention

The present invention is directed to a system and method of producing an undistorted dark field strain map of a semiconductor material at high spatial resolution through dark field electron holography.

2. Description of Related Art

Electron microscopes have been used extensively to look at structure at the nanometer scale. Most of the information obtained from electron microscopes is amplitude information. Yet, the phase information of electron microscopy, which can be obtained from off-axis electron holography, provides unique information on electronic structure and structural changes in a wide variety of materials. Monocrystalline silicon (Si) is used extensively in semiconductor devices, and has a diamond cubic crystal structure. Preferred electron flow direction in Si devices is along the <220> crystal direction. It is discovered that strain along this direction can either enhance or retard the current flow. For the semiconductor industry, junction profiling and strain mapping in silicon (Si) at high spatial resolution provide information that is critical for further scaling of semiconductor devices. Bright-field holography can measure the phase change of electrons traversing the materials, which is directly related to the mean inner potential of silicon, indicating the junction position at the nanometer scale. Furthermore, in recent years stressors have been incorporated into devices to change the semiconductor lattice constant in the channel region and thereby enhance hole and electron mobility. Like the junction definition, the extra processing steps involved to add strain in a device have increased development and manufacturing costs. One way to minimize development cycle time is to monitor, at a nanometer scale, changes in channel deformation resulting from process changes. Strain mapping along the <220> direction in Si provides channel strain information important to the semiconductor industry. For pFET, compressive strain improves device mobility; whereas for nFET, tensile strain improves device performance.

Dual-lens operation allows electron holography to be performed from low to high magnification and provides the field of view (FOV) and fringe spacing necessary for two-dimensional (2D) junction profiling and strain measurements for devices with various sizes. Prior art patents in this area include U.S. Pat. Nos. 7,015,469 and 7,102,145.

SUMMARY OF THE INVENTION

Bearing in mind the problems and deficiencies of the prior art, it is therefore a goal of the present invention to provide a system and method of producing an undistorted dark field strain map of a semiconductor material at high spatial resolution through dark field electron holography.

It is another goal of the present invention to provide improved, coma-free dark field holography interference images of the silicon employed in semiconductor devices.

Still other advantages of the invention will in part be obvious and will in part be apparent from the specification.

The present invention is directed to an inline dark field holographic method for measuring strain in a semiconductor or other crystalline material in which there is provided a transmission electron microscope having an electron gun for passing an electron beam along an axis through at least one specimen, a magnetic tilting coil for deflecting the beam at an angle with respect to the axis, first and second spaced objective lenses along the beam axis, and a biprism for combining a portion of the electron beam transmitted through the specimen with a portion bypassing the specimen. The method includes providing a condenser mini-lens between the magnetic tilting coil and the specimen for increasing defection of the beam at an angle with respect to the axis. The method then includes providing a pair of specimens of the semiconductor material, one specimen having a strained crystal structure to be measured and the other specimen having an unstrained crystal structure. The method further includes, with the magnetic tilting coil, deflecting the electron beam at an angle with respect to the axis; with the condenser mini-lens, deflecting the electron beam from the magnetic tilting coil at an additional, higher angle with respect to the axis prior to passing through the pair of specimens; with the first objective lens forming a virtual image of each of the specimens; with the second objective lens focusing the virtual images of each of the specimens at an intermediate image plane to form intermediate images of each of the specimens; and, with the biprism, causing the intermediate images of each of the specimens to overlap such that an interference pattern between the specimens is formed at the image plane. The interference pattern may then be viewed to determine the degree of strain of the strained specimen.

The method produces a dark field interference pattern that is substantially coma-free and which may have a resolution down to 1 nm. The strain may be measured along a <220> plane direction of a strained Si specimen.

The apertures of the first and second objective lens may be positioned along the axis of the beam. The first objective lens may be energized to a level less than one-half of maximum energy and the second objective lens may be energized to a level greater than one-half of maximum energy. The condenser mini-lens may tilt the limits of the beam to be greater than three times the angle of deflection of the magnetic tilting coil, with respect to the axis. For a 200 keV electron beam, this may be greater than 24 mrad with respect to the axis.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE EMBODIMENT(S)

In describing the embodiment(s) of the present invention, reference will be made herein to FIGS. 1-8 of the drawings in which like numerals refer to like features of the invention.

The electron passing through a specimen contains amplitude information as well as phase information. Regular transmission electron microscopy can only measure the amplitude information. However, electron holography can be used to measure both amplitude and phase information of the electron wave function passing through the sample. The electron holography is achieved by interfering two electron beams through a biprism: one electron beam passing through the region of interest and other electron beam passing through reference region.

To inspect the current generation of semiconductor devices, the requirements of electron holography are: (1) a fringe width (fringe overlap) in the range of about 100 to 800 nm for an adequate field of view (FOV), (2) fringe spacing between 0.5 and 5 nm for meaningful spatial resolution, (3) visibility of the fringe contrast (10-40%) for useful signal-to-noise ratio, and (4) adjustability of both the FOV and the fringe spacing relative to the sample.

The fringe spacing, $\sigma_i$, and fringe overlap, $W_i$, at the image plane are determined by the biprism voltage and have a limited range because of the requirement of fringe contrast value, $\mu$, for data processing [4-12]. Their relationship to the object (or specimen), $\sigma_o$ and $W_o$, can be written as:

$$\sigma_o = \sigma_i/M_o$$

and $$W_o = W_i/M_o$$

where $M_o$ is the magnification of the imaging lens(es). The equation shows that magnification is a dominant factor for the variation of fringe spacing and fringe overlap relative to the object.

The present invention is directed in particular to the use of dark field holography to produce an undistorted dark field interference or strain map of a semiconductor material at high spatial resolution. The principle of dark-field holography is to use a biprism to overlap a strained region of silicon (region of interest) in the device with an unstrained region of silicon (region of reference). The intensity of a dark-field hologram can be written as following:

$$I = A^2_{obj} + A^2_{ref} + 2\mu A_{obj} A_{ref} \cos[2\pi q_c \cdot r + 2\pi(g_{ref} - g_{obj}) \cdot r + \phi_{ref} - \phi_{obj}]$$

where $g_{obj}$ and $g_{ref}$ are g vectors from the region of the interest (object) and the region of the reference, respectively. The phase of the hologram is:

$$\phi = 2\pi(g_{ref} - g_{obj}) \cdot r + \phi_{ref} - \phi_{obj}$$

The lattice constant change to the first order can be approximated as:

$$\epsilon_{ii} = (d^{(i)}_{obj} - d^{(i)}_{ref})/d^{(i)}_{ref} \approx (g^{(i)}_{ref} - g^{(i)}_{obj})/g^{(i)}_{ref} \approx (\partial \phi^{(i)}/\partial r^i)/(2\pi g^{(i)}_{ref})$$

where i=x, y, g=1/d, and d is the lattice spacing. By selecting a specific diffracted beam with an objective aperture to obtain a dark-field hologram, the difference in lattice spacing between strained and unstrained Si can be measured.

Figure 1:
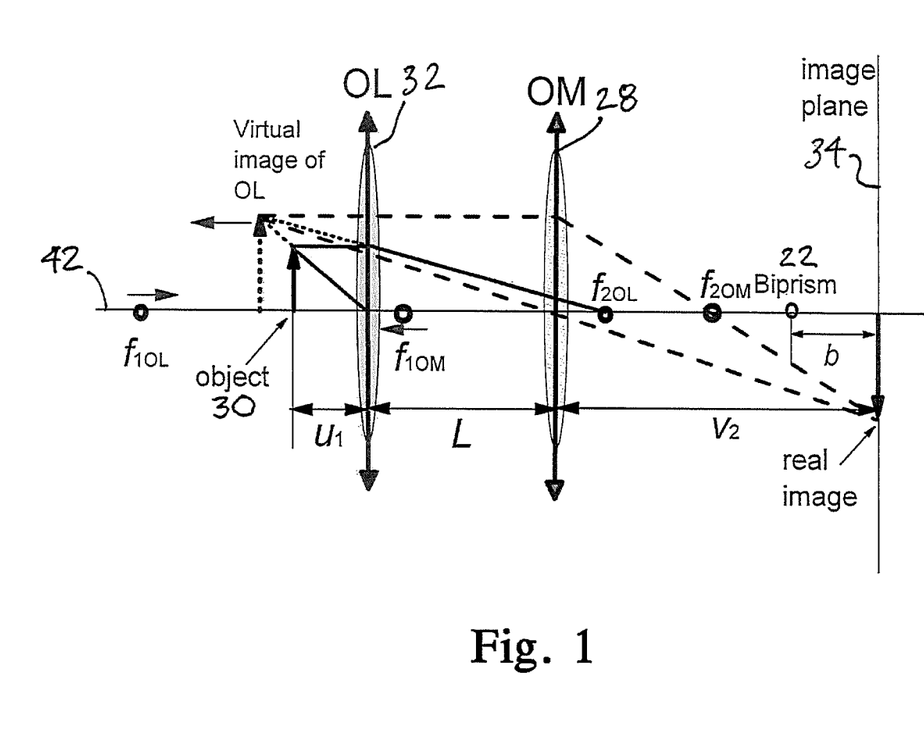
FIG. 1 is a side ray diagram of the dual lens portion (prior art U.S. Pat. No. 7,015,469) employed in the present invention.

FIG. 1 illustrates the electron optical ray diagram of a portion of the system useful to practice the present invention. A dual lens system may be employed which combines operation of the upper objective lens (OL) 32 and lower objective Lorentz or mini-lens (OM) 28, as used for the prior art dual-lens methodology and system for dark field strain mapping. The power (voltage or current) of OL 32 may be set so that the position of the specimen or object 30 is located behind the first focal point, $F_{OL}$, but before the lens OL 32, thereby forming a virtual image of the object. (The order or position given is with reference to the flow of the electron beam, which is normally in a downward direction from the electron gun. However, in FIG. 1, electron direction is from left to right.) The second objective lens (OM) 28 is used to project a real image of the virtual image of lens 32 (OL) to the intermediate image plane 34 located beyond the biprism. When the focal point of OL $F_{OL}$ gets closer to the sample, the virtual image moves further away from the sample and becomes more magnified. In order to refocus the OL virtual image onto the same image plane 34, the focal length of OM (lens 28) may be increased (i.e., the strength of OM is decreased) to compensate the movement of the virtual image position. The magnification of the sample at the image plane 34 may be adjusted by varying the focal length of the first objective lens (OL) to yield a virtual image of variable size which is then refocused to the intermediate image plane by the objective mini-lens (OM).

Using above mentioned method, thereby, the magnification of the sample at the image plane, $M_o$, can be adjusted by varying the focal length of the first objective lens (OL) to give a virtual image of variable size, which is refocused to the intermediate, image plane by the second objective lens (OM). By simultaneously operating the two lenses, the magnification may be changed without changing the position of the lenses. More specifically, by using both the first lens (OL) and the second lens (OM), the image of the first lens acts as the object of the second lens, so long as the final image plane is situated below the biprism.

Figure 2:
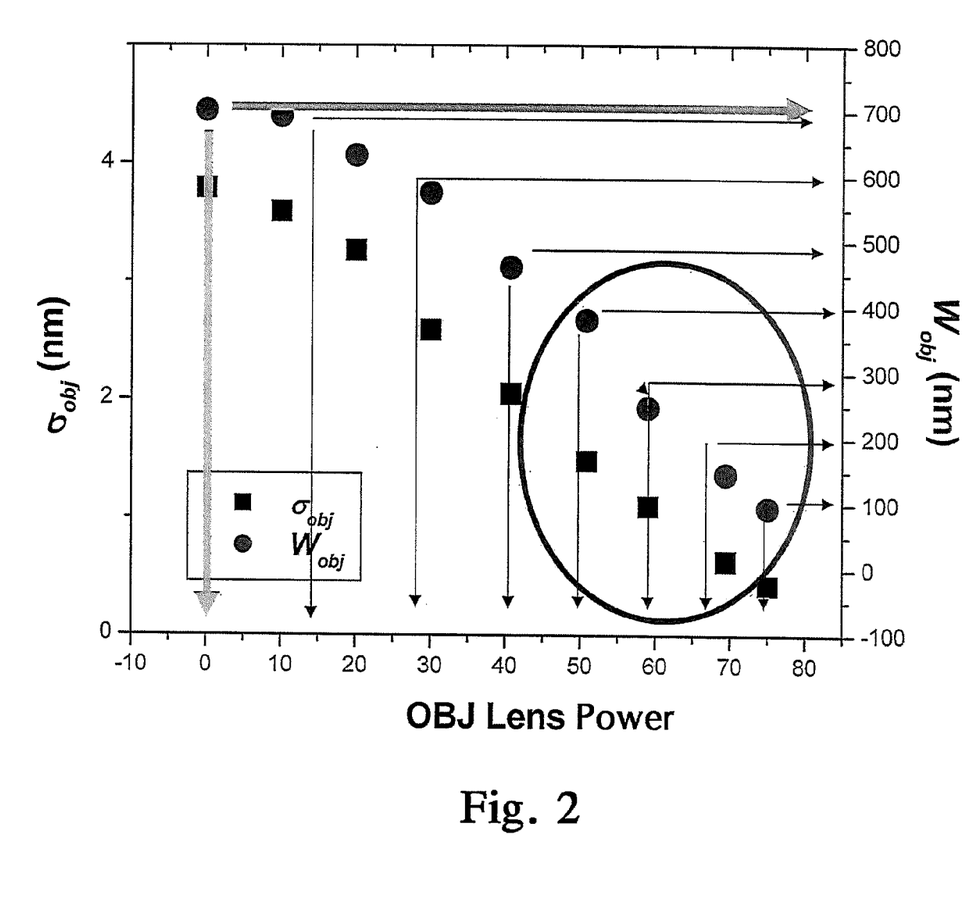
FIG. 2 is graphical representation of the effect of fringe spacing and fringe width or field of view as a function of the power of the first objective lens in a dual lens system of FIG. 1.

FIG. 2 is a graph of the effect of fringe spacing $\sigma_{obj}$ (squares) and fringe width or field of view $W_{obj}$ (circles) as a function of the first objective lens OL current (as a percentage of maximum power) for the dual lens system of FIG. 1. The dual lens system allows the field of view and spatial resolution to be adjustable by adjusting both the objective lens (lens 32) current and objective mini-lens (lens 28) current, with the field of ranging from 700 nm to 100 nm and fringe spacing range from ~4 nm to 0.5 nm. In the region where OL current is less than 40%, the field of view is larger than 400 nm and fringe spacing is larger than 2 nm. In this operating region (OL value between 0-40%), the beam tilt is limited to less than 8 mrad, which range is insufficient for the tilt of Si <220> diffracted beam as well as Si <004> diffracted beam to obtain dark field electron hologram without optical imaging distortion. For instance, to move Si <220> diffraction spot onto the optical axis, it requires tilt of 13 mrad for 200 keV electron beam. Likewise, to move Si <004> diffraction spot onto the optical axis, it requires beam tilt of 18.5 mrad. When OL lens current is larger than 50%, the field of view is smaller than 400 nm and fringe spacing is less than 2 nm. In this operating regime, as indicated by the region marked by an oval circle, the tilt limit of the incoming electron beam is increased to allow dark field imaging on both <220> diffracted beam as well as <004> diffracted beam. However, because of limited tilt in the operating region with an objective lens current range below 40%, the dark field tilt is insufficient to permit acceptable dark field holography of specimens such as strain mapping in Si. The present invention is directed in particular to operating this dual lens system so that power to the objective lens may be set at a relatively low power level, for example less than 40% of maximum, or even less than 30% of maximum, to obtain dark field electron hologram with large field of view, above the 400 nm to up to about 700 nm, without optical imaging distortion.

Figure 3:
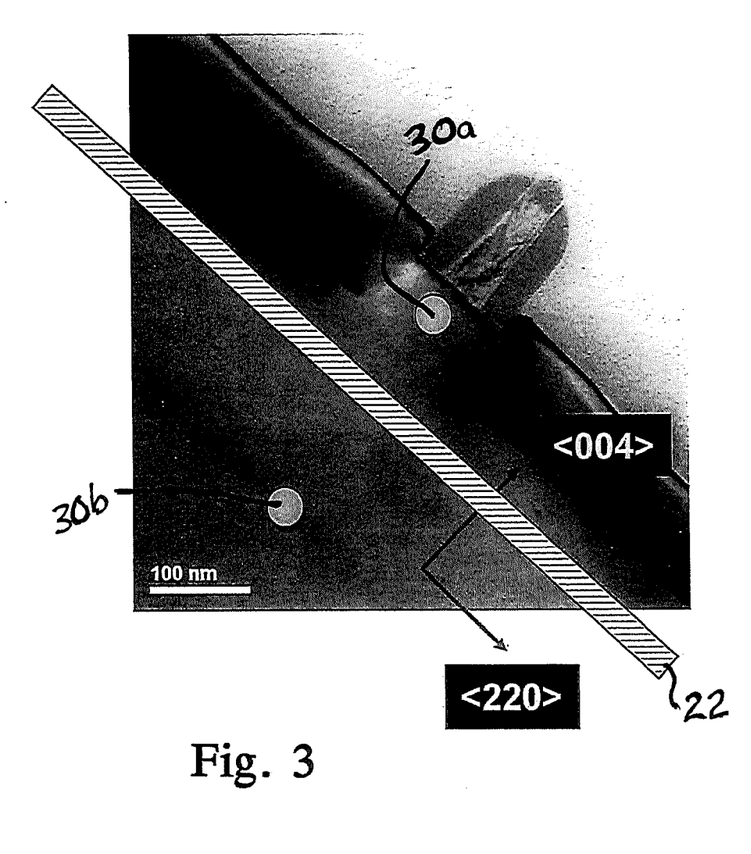
FIG. 3 is an illustration figure to show the region of interest and the region of reference divided by a biprism in the middle.
Figure 4:
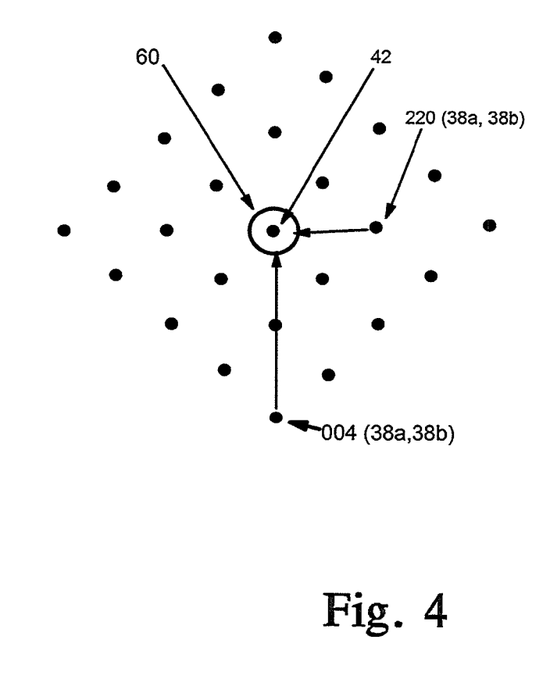
FIG. 4 is an image of the back focal plane showing the diffraction pattern of Si crystalline with <220> and <004> diffraction spots in the figure, moving into the objective aperture to form dark field images of <220> diffracted beam or <004> diffracted beam.
Figure 7:
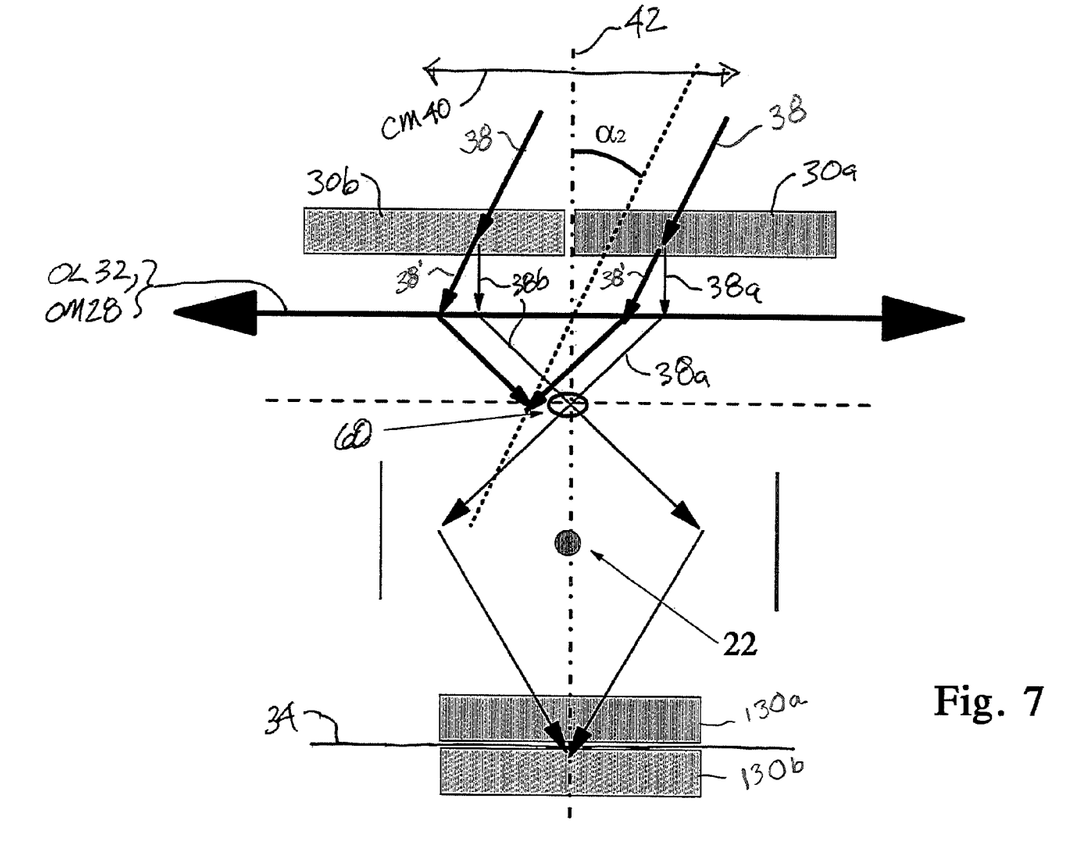
FIG. 7 is a side schematic diagram of a portion of the TEM of FIG. 5 showing the passage of diffracted electron beam portions as they pass through the strained and unstrained Si specimens, the dual objective lenses and the axially aligned objective aperture, and are overlapped by the biprism at the image plane to obtain the dark field holography image (interference pattern).
Figure 8:
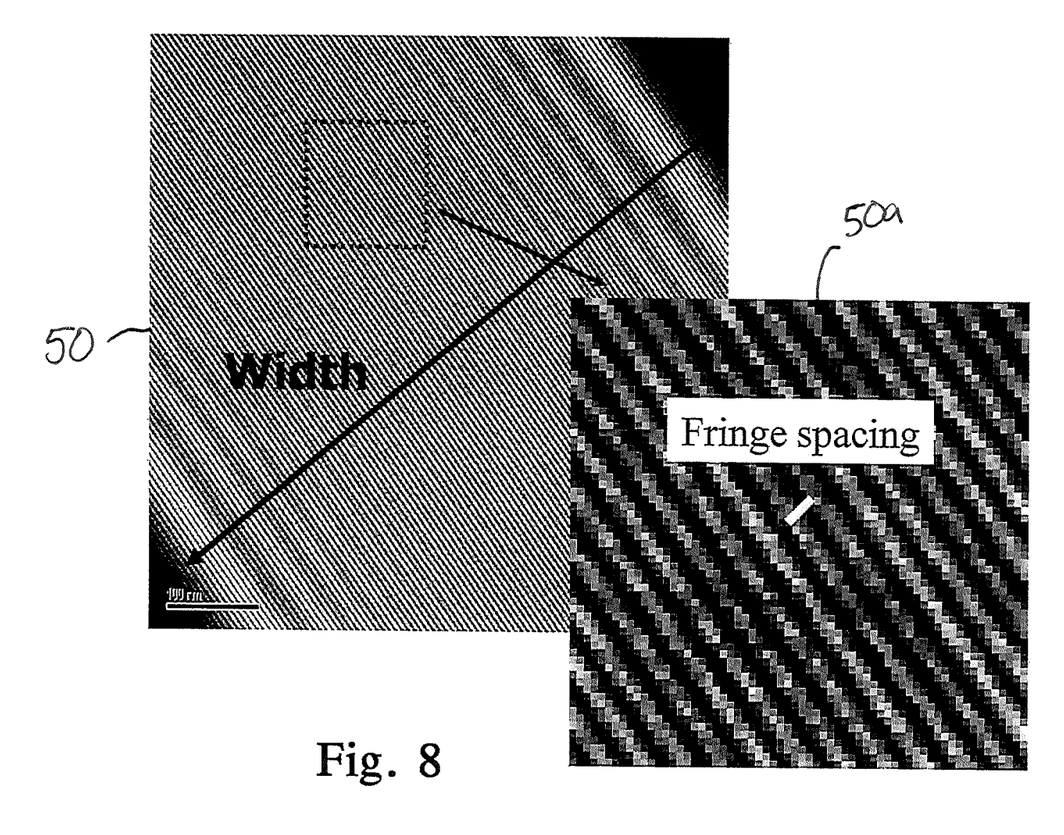
FIG. 8 is an electron hologram taken showing the interference pattern created between region of interesting and region of reference, and the measurement of fringe spacing in an enlarged inset.

In dark field holography, the incoming electron beam is tilted or deflected from its normal axis, passed through the specimen, and an image is formed using a diffracted beam of interest. For the aforementioned Si material, the <220> diffraction beam is used to measure strain in the direction of current (electron) flow $\sigma_{xx}$ and the <004> diffraction beam is used to measure strain perpendicular to that $\sigma_{yy}$. The deflected electron beam is passed through strained and unstrained Si specimens placed side-by-side, and a biprism is placed downstream to overlap the images to create the interference pattern between the strained and unstrained images (FIG. 3, FIG. 4, FIG. 7). The objective aperture 60 and offset diffraction patterns of the <220> and <004> planes created by the image at the back focal plane is shown in FIG. 4. The present invention provides a method of centering the <220> and <004> diffracted beam into objective aperture 60 located along the optical axis 42.

Figure 5:
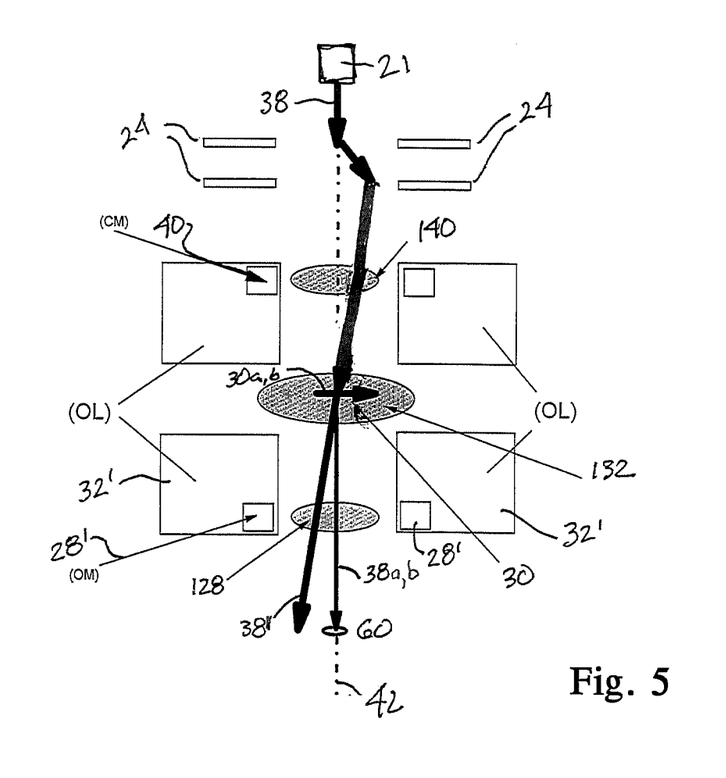
FIG. 5 is a side schematic diagram of a transmission electron microscope (TEM) set up to practice the method of using dark field holography to determine strain of a semiconductor material employed in the present invention.

A transmission electron microscope (TEM) 20 for employing the method of the present invention is shown in FIG. 5 having an electron gun 21, a beam tilting coil 24 and a specimen holder on which are placed silicon specimens 30a and 30b. Specimen 30a is of the strained silicon to be measured, and specimen 30b is of a comparable but unstrained silicon. Below the specimens are coils 32' that create the magnetic field of the first objective lens OL and coils 28' that create the magnetic field of the second or Lorentz objective lens OM. Although the coils 28' and 32' are shown superimposed, the magnetic field lenses produced are in the same sequence and have the same function as shown in FIG. 1, with objective lens OL very close to the specimen, and the second objective or Lorentz lens (OM) beyond and below the OL. An electron biprism 22 is positioned below and beyond OL 28', and below and beyond that an imager 36 such as an observation or recording device for viewing the projection of the images, 130a and 130b, which is the overlay interference images of the specimens 30a, 30b, respectively. Between the image plane 34 and device 36, there are projection lenses (normally four electron magnetic lenses—not shown) to magnify the overlay interference images of 130a and 130b further and project the images onto device 36. The observation/recording device 36 may be, for example, a fluorescent screen, a photography device, or a TV camera.

In accordance with the method of the present invention, a third lens 40 is provided between the beam tilting coil 24 and the holder for specimens 30a, 30b to magnify the tilt and further deflect the electron beam after it passes through the tilting coil. The third lens 40 may be the condenser mini-lens (CM) in a twin lens system sold by FEI Corporation. The third lens or CM 40 may be energized at power (voltage or current) levels in the range of about 25 to 75% of maximum power, for example about 60% of maximum, while the objective lens OL is at the aforementioned low power levels, for example, from 0 to about 40% of maximum power, to provide additional tilt to the electron beam while achieving maximum field of view for the system 20. With the first objective lens power OL at a relatively low level, the power to the second objective lens OM may be increased. Energy of condenser lenses above the condenser mini-lens may be changed accordingly to satisfy parallel illumination by the beam.

Figure 6:
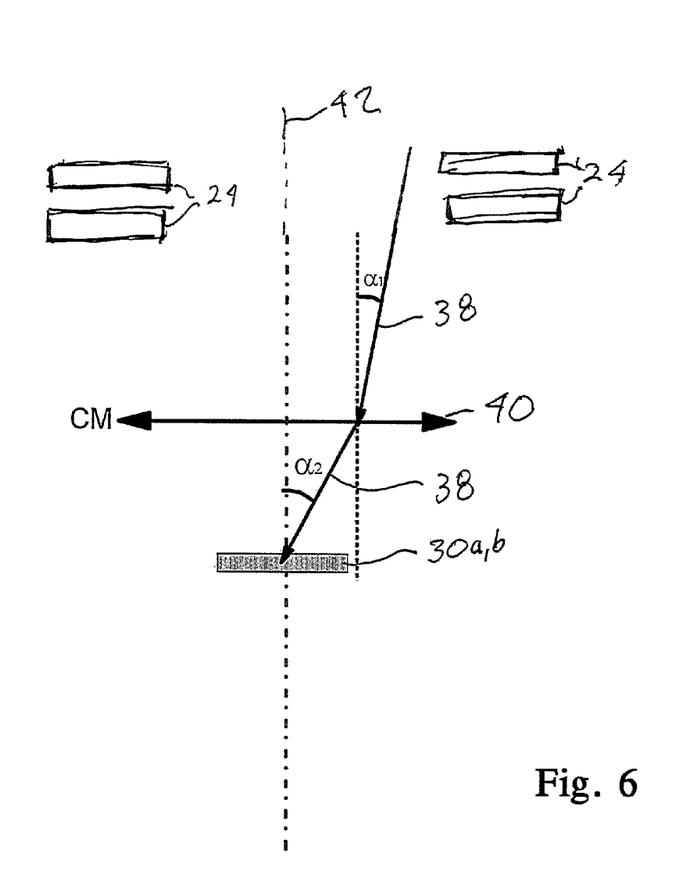
FIG. 6 is a side schematic diagram of a portion of the TEM of FIG. 5 showing the further deflection of the electron beam as it passes through the condenser mini-lens (CM).

As shown in FIG. 5, electron beams 38 is emitted from electron gun 21 parallel to and along optical axis 42. As the un-diffracted beam passes tilting magnetic coils 24, it changes direction toward axis 42 at a first angle $\alpha_1$, which is typically less than 8 mrads. As the beam 38 then passes through the magnetic field 140 of third lens or CM 40, it is further deflected and directed inward toward axis 42, at a greater angle $\alpha_2$ with respect to axis 42, up to three (3) times or more than the original tilt angle limit, typically more than 24 mrad, as shown in FIG. 6. While these angles are typical for an electron beam energy of about 200 keV, they may change if the energy is higher or lower, for example 100 keV or 300 keV. The beam 38 diffracted through specimens 30a, 30b continues along and parallel to axis 42, while un-diffracted beam 38' continues onward at angle $\alpha_2$, as shown in FIG. 5. The deflected electron beam beyond and below third lens 40 is shown in FIG. 7 as parallel beam portions 38a and 38b that pass through side-by-side strained Si specimen 30a and unstrained Si specimen 30b, respectively, and continue onward as diffracted beam portions as they are focused by the magnetic field 132 of objective lens OL 32' and the magnetic field 128 of Lorentz objective lens OM 28' on axis 42. The effect is to move the virtual source of the electron beam to a higher angle laterally away from the center of the optical axis, which allows diffracted beam (38a and 38b) to be moved into objective aperture 60 along the back focal plane, which is on the optical axis 42. Unlike other prior art systems, where the beam tilt limit is smaller, the present invention does not require that the apertures 60 to be moved to the diffracted beam position which would be off optical axis 42 to form a dark field hologram. The dark field hologram with off-optical axis by moving objective aperture 60 away from optical axis 42 would contain optical distorted (coma) dark field image, which results in distorted strain image.

After passing through electric biprism 22, the diffracted beams 38a, 38b are then directed toward axis 42 so that the waves interfere and the image 130a of specimen 30a and the image 130b of specimen 30b overlap at the image plane 34. The overlapping, interfering images produce an interference pattern 50 between the two images (FIG. 8), from which fringe spacing 52 may be determined from a close-up inspection 50a. The degree of strain on the strained Si specimen 30a may then be determined by well-known data processing method known as Fast Fourier Transformation (FFT) and inverse Fast Fourier Transformation ($FFT^{-1}$) of selected sideband to obtain the derivative of the phase ($\phi$) as shown in the equations mentioned above.

The degree of deflection or tilt that may be achieved for the electron beam as it passes through the specimens is greater than that which may be achieved by the otherwise conventional beam tilting coils of the prior art, and has been found to be particularly effective and useful when the objective lens OL power is reduced to less 40%. The additional benefit of the present invention is that fringe spacing and fringe width is increased, providing a greater field of view of the specimen.

The present invention is therefore able to provide improved, coma-free dark field holography interference images of the specimens, which results in undistorted dark field strain map of the semiconductor material at high spatial resolution through dark field electron holography.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. An inline dark field holographic method for measuring strain in a semiconductor material or other crystalline materials comprising:
   providing a transmission electron microscope having an electron gun for passing an electron beam along an axis through at least one specimen, a magnetic tilting coil for deflecting the beam at an angle with respect to the axis, first and second spaced objective lenses along the beam axis, and a biprism for combining a portion of the electron beam transmitted through the specimen with a portion bypassing the specimen;
   providing a condenser mini-lens between the magnetic tilting coil and the specimen for increasing defection of the beam at an angle with respect to the axis;
   providing a pair of specimens of the semiconductor material, one specimen having a strained crystal structure to be measured and the other specimen having an unstrained crystal structure;
   with the magnetic tilting coil, deflecting the electron beam at an angle with respect to the axis;
   with the condenser mini-lens, deflecting the electron beam from the magnetic tilting coil at an additional, higher angle with respect to the axis prior to passing through the pair of specimens;
   with the first objective lens forming a virtual image of each of the specimens;
   with the second objective lens focusing the virtual images of each of the specimens at an intermediate image plane to form intermediate images of each of the specimens;
   with the biprism, causing the intermediate images of each of the specimens to overlap such that an interference pattern between the specimens is formed at the image plane; and
   viewing the interference pattern and determining the degree of strain of the strained specimen.

2. The method of claim 1 wherein the dark field interference pattern is substantially coma-free.

3. The method of claim 1 wherein the dark field interference pattern has a resolution down to 1 nm.

4. The method of claim 1 wherein the first objective lens is energized to a level less than one-half of maximum energy.

5. The method of claim 1 wherein the second objective lens is energized to a level greater than one-half of maximum energy.

6. The method of claim 1 wherein the strain is measured along a <220> plane direction of the strained specimen.

7. The method of claim 1 wherein the condenser mini-lens tilts limits of the beam to be greater than three times the angle of deflection of the magnetic tilting coil, with respect to the axis.

8. The method of claim 1 wherein the condenser mini-lens tilts limits of the beam to be greater than 24 mrad with respect to the axis.

9. The method of claim 1 wherein apertures of the first and second objective lens are positioned along the axis of the beam.

10. An inline dark field holographic method for measuring strain in a semiconductor material or other crystalline materials comprising:
    providing a transmission electron microscope having an electron gun for passing an electron beam along an axis through at least one specimen, a magnetic tilting coil for deflecting the beam at an angle with respect to the axis, first and second spaced objective lenses along the beam axis, and a biprism for combining a portion of the electron beam transmitted through the specimen with a portion bypassing the specimen;
    providing a condenser mini-lens between the magnetic tilting coil and the specimen for increasing defection of the beam at an angle with respect to the axis;
    providing a pair of specimens of the semiconductor material, one specimen having a strained crystal structure to be measured and the other specimen having an unstrained crystal structure;
    with the magnetic tilting coil, deflecting the electron beam at an angle with respect to the axis;
    with the condenser mini-lens, deflecting the electron beam from the magnetic tilting coil at an additional, higher angle with respect to the axis prior to pass through the pair of specimens;
    positioning apertures of the first and second objective lens along the axis of the beam;
    with the first objective lens forming a virtual image of each of the specimens;
    with the second objective lens focusing the virtual images of each of the specimens at an intermediate image plane to form intermediate images of each of the specimens;
    with the biprism, causing the intermediate images of each of the specimens to overlap such that an interference pattern between the specimens is formed at the image plane; and
    viewing the interference pattern and determining the degree of strain of the strained specimen.

11. The method of claim 10 wherein the dark field interference pattern is substantially coma-free and has a resolution down to 1 nm.

12. The method of claim 10 wherein the second objective lens is energized to a level greater than one-half of maximum energy.

13. The method of claim 10 wherein the strain is measured along a <220> plane direction of the strained specimen.

14. The method of claim 10 wherein the condenser mini-lens tilts limits of the beam to be greater than three times the angle of deflection of the magnetic tilting coil, with respect to the axis.

15. The method of claim 10 wherein the condenser mini-lens tilts limits of the beam to be greater than 24 mrad with respect to the axis.

16. An inline dark field holographic method for measuring strain in a semiconductor material or other crystalline materials comprising:
   providing a transmission electron microscope having an electron gun for passing an electron beam along an axis through at least one specimen, a magnetic tilting coil for deflecting the beam at an angle with respect to the axis, first and second spaced objective lenses along the beam axis, and a biprism for combining a portion of the electron beam transmitted through the specimen with a portion bypassing the specimen;
   providing a condenser mini-lens between the magnetic tilting coil and the specimen for increasing deflection of the beam at an angle with respect to the axis;
   providing a pair of specimens of the semiconductor material, one specimen having a strained crystal structure to be measured and the other specimen having an unstrained crystal structure;
   energizing the first objective lens is to a level less than one-half of maximum energy;
   energizing the second objective lens is to a level greater than one-half of maximum energy;
   with the magnetic tilting coil, deflecting the electron beam at a first angle with respect to the axis;
   with the condenser mini-lens, deflecting the electron beam from the magnetic tilting coil at a second angle at least three time greater than the first angle with respect to the axis prior to passing through the pair of specimens;
   with the first objective lens forming a virtual image of each of the specimens;
   with the second objective lens focusing the virtual images of each of the specimens at an intermediate image plane to form intermediate images of each of the specimens;
   with the biprism, causing the intermediate images of each of the specimens to overlap such that an interference pattern between the specimens is formed at the image plane; and
   viewing the interference pattern and determining the degree of strain of the strained specimen.

17. The method of claim 16 wherein the dark field interference pattern is substantially coma-free and has a resolution down to 1 nm.

18. The method of claim 16 wherein the strain is measured along a <220> plane direction of the strained specimen.

19. The method of claim 16 wherein the condenser mini-lens tilts limits of the beam to be greater than 24 mrad with respect to the axis.

20. The method of claim 16 wherein apertures of the first and second objective lens are positioned along the axis of the beam.

* * * * *